United States Patent [19]

Angrick et al.

[11] Patent Number: 4,619,701
[45] Date of Patent: Oct. 28, 1986

[54] ISOLATING AGENT

[75] Inventors: Michael Angrick, Berlin; Martin-Willi Späth, Wehrheim, both of Fed. Rep. of Germany

[73] Assignee: Kulzer & Co. GmbH, Wehrheim, Fed. Rep. of Germany

[21] Appl. No.: 723,738

[22] Filed: Apr. 16, 1985

[30] Foreign Application Priority Data

Jul. 4, 1984 [DE] Fed. Rep. of Germany ....... 3424538

[51] Int. Cl.⁴ .............................................. B28B 7/36
[52] U.S. Cl. .................................. 106/38.23; 106/208
[58] Field of Search .............................. 106/38.23, 208

[56] References Cited

U.S. PATENT DOCUMENTS 2,780,555  2/1957  Budewitz ............................ 106/208
3,287,143  11/1966  Yavorsky ............................... 501/94

OTHER PUBLICATIONS

Chem. Abst. 68:6163f, Stambolieva, 1967.
Chem. Abst. 96:110,192d, Paniti, 1977.

Primary Examiner—Theodore Morris

[57] ABSTRACT

Isolating agents consisting of aqueous alginate solutions which contain preservatives and have a pH between 5.5 and 8.5 are stable in storage and have uniformly good working properties even after a long period of storage. They are suitable for isolating the surface of plaster molds against plastic.

6 Claims, 8 Drawing Figures

FIG. 1 EXAMPLE 2
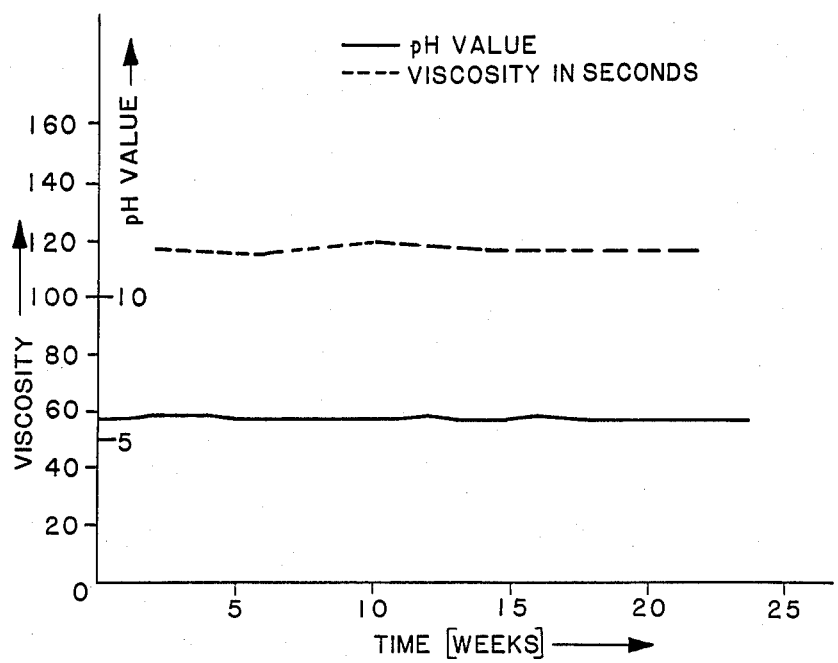
FIG. 2 EXAMPLE 3
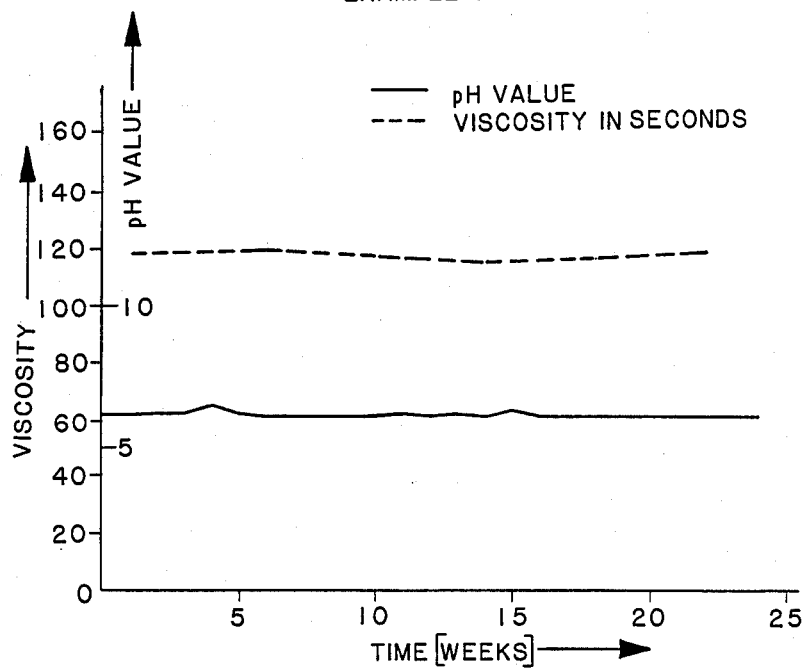

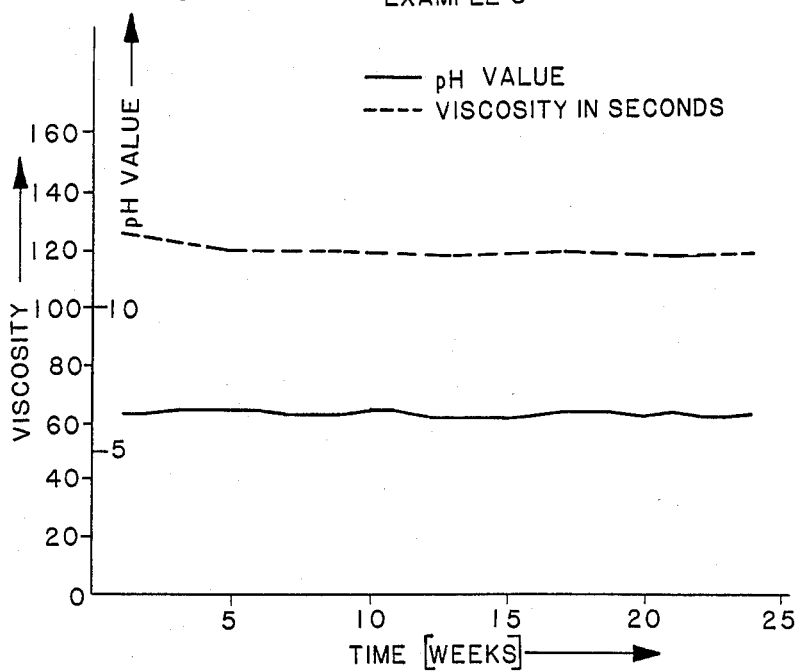
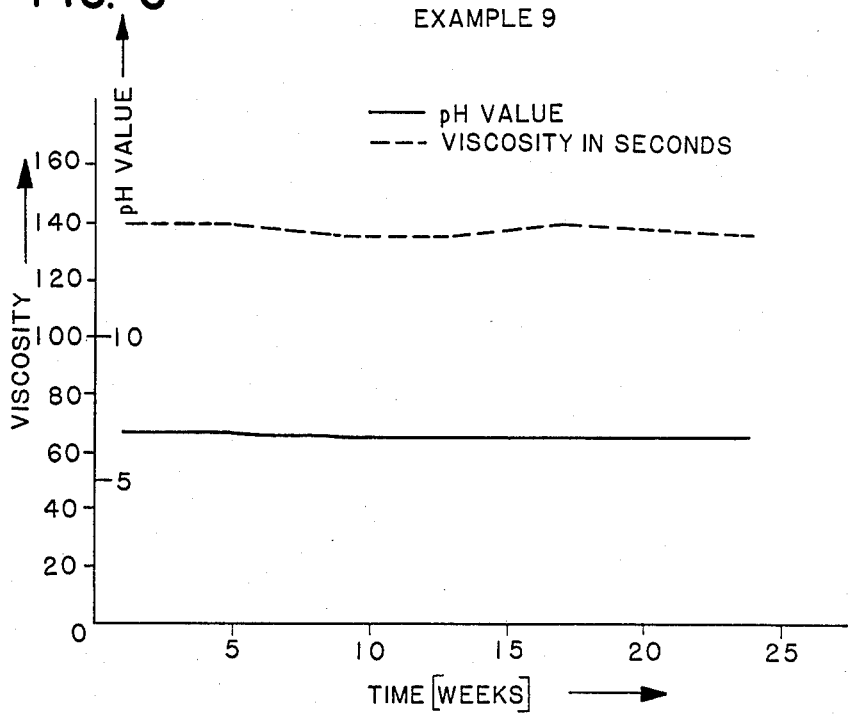

ISOLATING AGENT

BACKGROUND OF THE INVENTION

The invention relates to an isolating agent consisting of an aqueous alginate solution containing a preservative.

In the preparation of plastic dental prostheses and parts for dental restoration, isolating agents composed of thin aqueous solutions of soluble alginates are often used to isolate the plaster surface from the plastic.

An isolating agent of this kind is described, for example, in German Pat. No. 811,713. It consists of an aqueous solution of sodium or potassium alginate, which can also contain glycerin or another hygroscopic substance if desired.

DESCRIPTION OF PRIOR ART

The keeping qualities of isolating agent solutions can be improved by the addition of preservatives (German Pat. No. 837,147; Rumanian Pat. No. 71,677, reported in CA 96, 110192; Stomatologiya, Sofia, 49, 344-53, 1967, reported in CA 68, 6163).

To enable plastic dentures to be separated easily from the plaster mold, it is proposed in German Pat. No. 966,997 to use alginate solutions containing water-soluble amines. The forming of films by these amine-alginate solutions on the plaster surface can be retarded by the addition of, for example, sodium carbonate, which is also contained in alginate impression materials as a so-called retardant.

It is the object of the invention to find an aqueous solution of an alginate which will be suitable for the isolation of the plaster surface against the plastic of dental prostheses and against attack by microorganisms, and which will have a long shelf life.

THE INVENTION

The isolating agents of this invention comprise aqueous alginate solutions, a preservative, and a buffer mixture, at a pH from about 6.5 to about 8.5.

Mixtures of citric acid and sodium hydroxide (pH 6.5), mixtures of glycine and sodium hydroxide (pH 8), and mixtures of disodium hydrogen phosphate dihydrate and potassium dihydrogen phosphate (pH 8.5) have proven especially valuable buffer mixtures.

Isolating agents of the invention have excellent keeping qualities and shelf life, and retain their good working properties even after long periods of storage. The viscosity and pH of the isolating agents remain virtually constant for a long time.

To activate the plaster surface and prevent any white discoloration of the plastic, it has been found desirable to add to the isolating agent a water-soluble copper (II) salt, e.g., copper (II) chloride, preferably in an amount of 0.1 to 0.2% by weight, and to add in some cases a water-soluble salt a barbituric acid or barbituric acid derivative, such as for example the sodium salt of 5-phenylbarbituric acid, preferably in an amount of about 0.5% by weight.

The isolating agent contains one or more of the preservatives known for this purpose, such as for example benzoic acid or benzoates, p-hydroxybenzoic acid esters (PHB esters), phenols, sorbic acid and its salts, formalin, hexetidin, sodium salicylate and neomycin sulfate, in an amount sufficient for protection against attack by microorganisms.

The isolating agents are 2 to 5 percent, preferably 2 to 3 percent, aqueous solutions of sodium, potassium or ammonium alginates.

BRIEF DESCRIPTION OF THE FIGURES

FIGS. 1–8 set forth, graphically, pH and viscosity changes in relation to time for Examples 2-4, 7-9 and Isolating Solutions 1 and 2.

EXAMPLES

Figure 3:
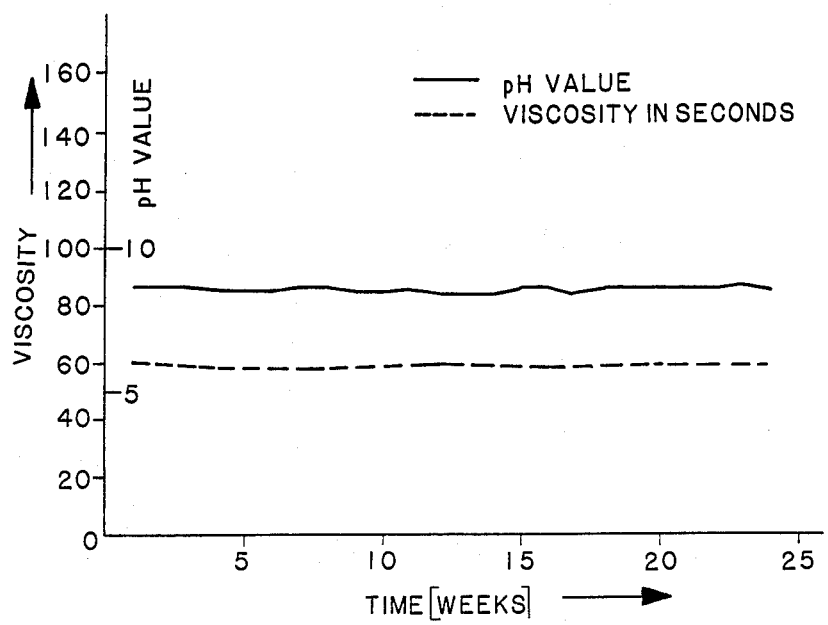

To further explain the invention, isolating agents in accordance with the invention are described in the following examples.

Example 1

| Isolating Agent with a pH of 8.5 | |
|---|---|
| 96.2 weight-percent | water |
| 2.6 weight-percent | alginate (Manucol FH made by Alginat Industries GmbH, Hamburg) |
| 1 weight-percent | disodium hydrogen phosphate dihydrate |
| 0.1 weight-percent | potassium dihydrogen phosphate |
| 0.1 weight-percent | neomycin sulfate |

Example 2

| Isolating Agent with a pH of 6 | |
|---|---|
| 95.26 weight-percent | water |
| 0.6 weight-percent | sodium hydroxide |
| 1 weight-percent | citric acid |
| 0.1 weight-percent | copper(II) chloride |
| 2.6 weight-percent | alginate (Manucol FH of Alginat Industries GmbH, Hamburg) |
| 0.2 weight-percent | sodium pyrophosphate |
| 0.12 weight-percent | sorbic acid |
| 0.12 weight-percent | formalin, 37% solution |

Example 3

| Isolating Agent with a pH of 6.5 | |
|---|---|
| 95.38 weight-percent | water |
| 0.6 weight-percent | sodium hydroxide |
| 1 weight-percent | citric acid |
| 0.1 weight-percent | copper(II) chloride |
| 2.6 weight-percent | Alginate (Manucol FH of Alginat Industries GmbH, Hamburg) |
| 0.2 weight-percent | sodium pyrophosphate |
| 0.12 weight-percent | formalin, 37% solution |

Example 4

| Isolating Agent with a pH of 8.5 | |
|---|---|
| 95.9 weight-percent | water |
| 2.6 weight-percent | alginate (Manucol FH of Alginat Industries GmbH., Hamburg) |
| 1 weight-percent | disodium hydrogen phosphate dihydrate |
| 0.1 weight-percent | potassium dihydrogen phosphate |
| 0.2 weight-percent | sodium pyrophosphate |
| 0.1 weight-percent | copper(II) chloride |
| 0.1 weight-percent | neomycin sulfate |

Example 5

| Isolating Agent with a pH of 6.5 | |
|---|---|
| 95.4 weight percent | water |

Isolating Agent with a pH of 6.5

| | |
|---|---|
| 2.6 weight-percent | alginate (Manucol FH of Alginat Industries GmbH., Hamburg) |
| 1 weight-percent | citric acid |
| 0.6 weight-percent | sodium hydroxide |
| 0.2 weight-percent | sodium pyrophosphate |
| 0.1 weight-percent | copper(II) chloride |
| 0.1 weight-percent | neomycin sulfate |

Example 6

Isolating Agent with a pH of 8

| | |
|---|---|
| 95.78 weight-percent | water |
| 0.7 weight-percent | glycine |
| 0.5 weight-percent | sodium chloride |
| 0.02 weight-percent | sodium hydroxide |
| 2.6 weight-percent | alginate (Manucol FH of Alginat Industries GmbH, Hamburg) |
| 0.2 weight-percent | sodium pyrophosphate |
| 0.1 weight-percent | copper(II) chloride |
| 0.1 weight-percent | neomycin sulfate |

Example 7

Isolating Agent with a pH of 8

| | |
|---|---|
| 95.24 weight-percent | water |
| 0.05 weight-percent | sodium hydroxide |
| 0.63 weight-percent | glycine |
| 0.49 weight-percent | sodium chloride |
| 0.51 weight-percent | sodium salt of 5-phenylbarbituric acid |
| 0.13 weight-percent | copper(II) chloride |
| 2.64 weight-percent | alginate (Manucol FH of Alginat Industries GmbH, Hamburg) |
| 0.2 weight-percent | sodium pyrophosphate |
| 0.11 weight-percent | formalin, 37% solution |

Example 8

Isolating Agent with a pH of 6.5

| | |
|---|---|
| 94.84 weight-percent | water |
| 0.58 weight-percent | sodium hydroxide |
| 1.01 weight-percent | citric acid |
| 0.51 weight-percent | sodium salt of 5-phenylbarbituric acid |
| 0.13 weight-percent | copper(II) chloride |
| 0.20 weight-percent | sodium pyrophosphate |
| 2.62 weight-percent | alginate (Manucol FH of Alginat Industries GmbH, Hamburg) |
| 0.11 weight-percent | formalin, 37% solution |

Example 9

Isolating Agent with a PH of 6.5

| | |
|---|---|
| 95.19 weight-percent | water |
| 0.67 weight-percent | glycine |
| 0.02 weight-percent | sodium hydroxide |
| 0.55 weight-percent | sodium chloride |
| 0.5 weight-percent | sodium salt of 5-phenylbarbituric acid |
| 0.13 weight-percent | copper(II) chloride |
| 2.63 weight-percent | alginate (Manucol FH of Alginat Industries GmbH, Hamburg) |
| 0.2 weight-percent | sodium pyrophosphate |
| 0.11 weight-percent | formalin, 37% solution |

Isolating Solution 1 (Comparison, without buffer mixture)

| | |
|---|---|
| 97.48 weight-percent | water |
| 2.4 weight-percent | alginate (manucol FH of Alginat Industries GmbH, Hamburg) |
| 0.12 weight-percent | formalin, 37% solution |

Isolating Solution 2 (Comparison, without preservative)

| | |
|---|---|
| 95.5 weight-percent | water |
| 0.6 weight-percent | sodium hydroxide |
| 1.0 weight-percent | citric acid |
| 0.1 weight-percent | copper(II) chloride |
| 2.6 weight-percent | alginate (Manucol FH of Alginat Industries GmbH, Hamburg) |
| 0.2 weight-percent | sodium pyrophosphate |

Figure 4:
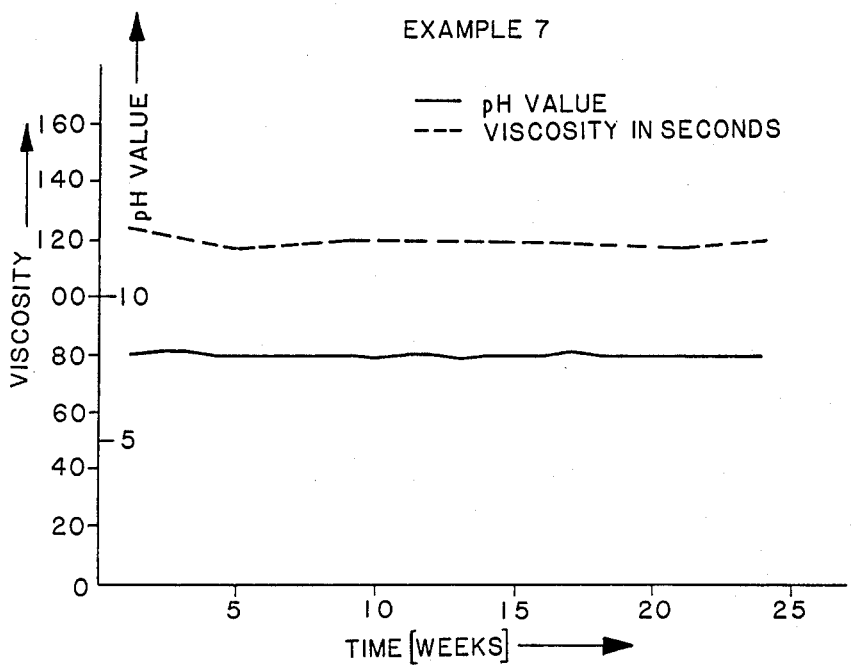
Figure 7:
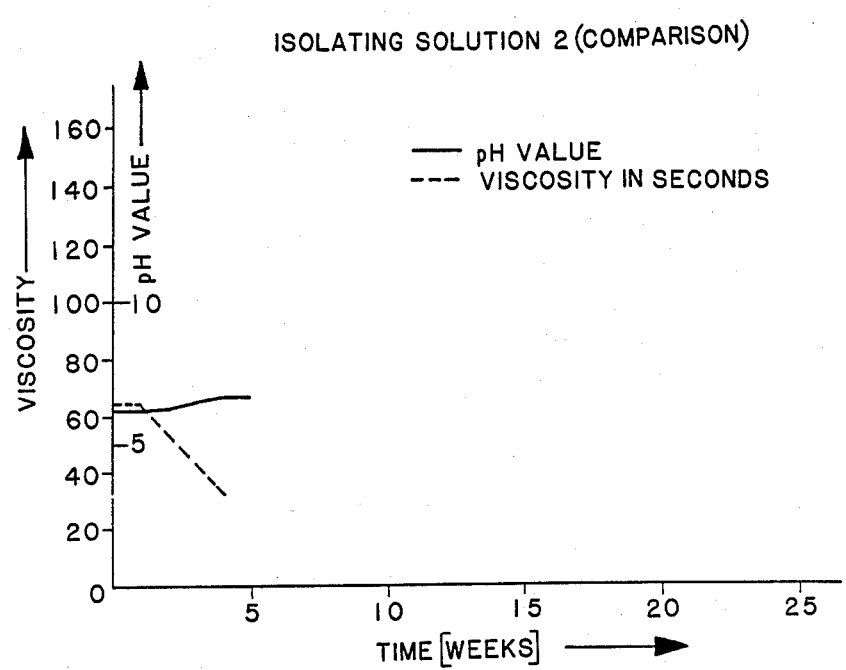
Figure 8:
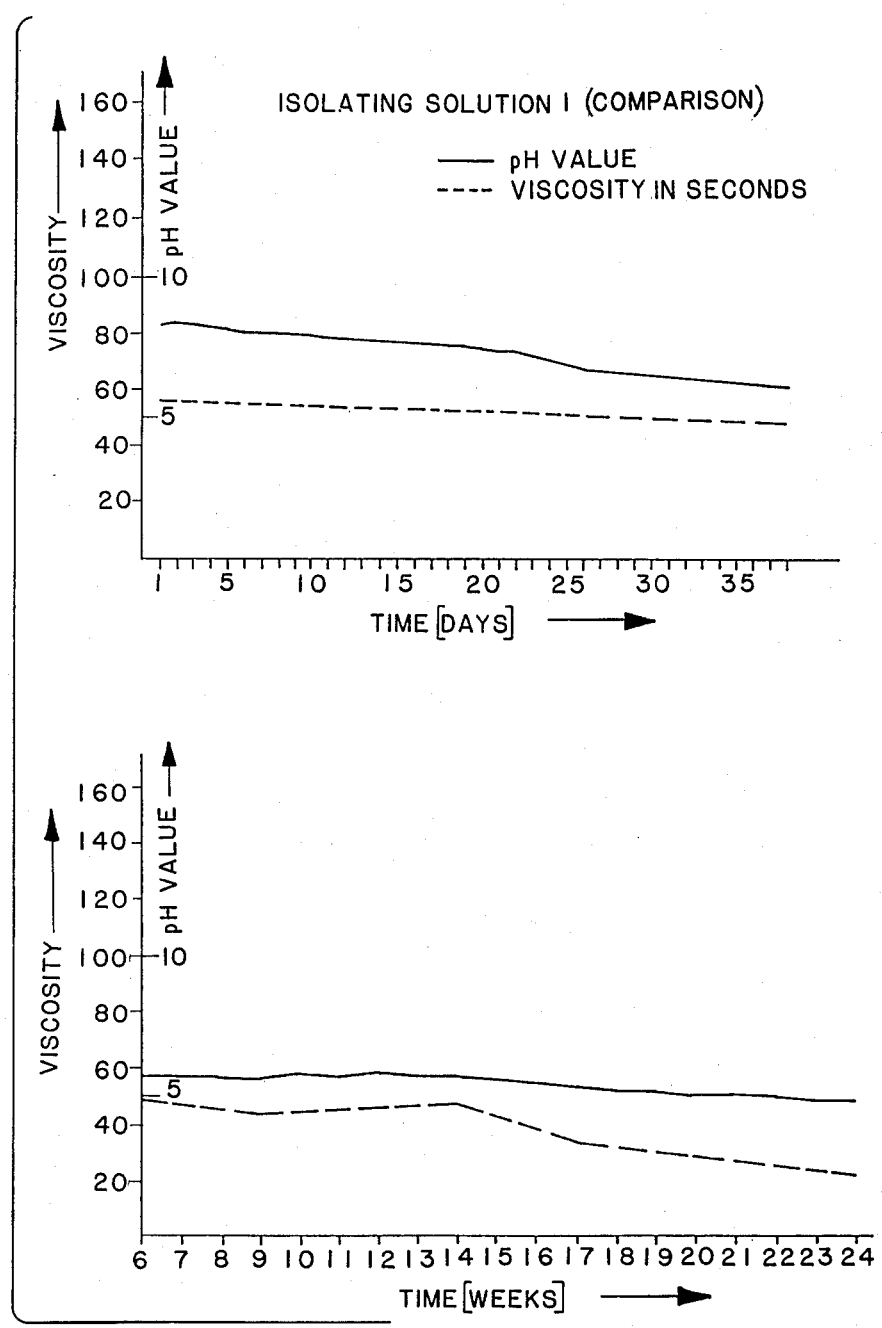

The changes in the pH and in the viscosity (determined as the pouring time in seconds, measured with the Ford cup) of the isolating agents described in Examples 2, 3, 4, 7, 8 and 9, and of the isolating solutions 1 (without buffer mixture) and 2 (without preservative), were studied in relation to time. The pH and viscosity changes in relation to time are represented graphically in FIGS. 1 to 8. The experiment with isolating solution 2, which contained no preservative, had to be discontinued after 6 weeks on account of the formation of molds.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolating agent of an aqueous alginate solution containing a preservative and a buffer with a pH between 5.5 and 8.5, characterized in that the buffer mixture consists of glycine and sodium hydroxide.

2. Isolating agent of an aqueous alginate solution containing a preservative and a buffer with a pH between 5.5 and 8.5 characterized in that the buffer mixture consists of disodium hydrogen phosphate dihydrate and potassium dihydrogen phosphate.

3. Isolating agent of claim 1 wherein said agent contains a water soluble copper (II) salt.

4. Isolating agent of claim 1 wherein said agent contains a water soluble copper (II) salt and a 5. Isolating agent of claim 4, wherein said agent contains the sodium salt of 5-phenylbarbituric acid.

6. Isolating agent of claim 3 wherein said agent contains copper (II) chloride.

* * * * *